United States Patent

Corbin et al.

[11] Patent Number: 6,040,486
[45] Date of Patent: Mar. 21, 2000

[54] PROCESS FOR THE MANUFACTURE OF 2-CHLORO-1,1,1-TRIFLUOROETHANE

[75] Inventors: David Richard Corbin, West Chester, Pa.; V. N. Mallikarjuna Rao, Wilmington, Del.

[73] Assignee: E. I. du Pont de Nemours and Company, Wilmington, Del.

[21] Appl. No.: 08/167,656

[22] Filed: Dec. 20, 1993

Related U.S. Application Data

[63] Continuation of application No. 07/672,875, Mar. 20, 1991, abandoned.

[51] Int. Cl.[7] .................................................. C07C 17/08
[52] U.S. Cl. ................................................ 570/168
[58] Field of Search ............................................. 570/168

[56] References Cited

U.S. PATENT DOCUMENTS

| | | | |
|---|---|---|---|
| 1,996,115 | 4/1935 | Lazier | 570/168 |
| 3,178,483 | 4/1965 | Christoph et al. | 260/653.4 |
| 3,178,484 | 4/1965 | Christoph et al. | 260/653.4 |
| 3,591,646 | 7/1971 | Vecchio et al. | 260/653.6 |
| 3,607,955 | 9/1971 | Gardner | 260/653.5 |
| 3,728,405 | 4/1973 | Thoroughgood | 260/648 F |
| 3,793,229 | 2/1974 | Gropelli et al. | 570/168 |
| 4,766,259 | 8/1988 | Manzer et al. | 570/168 |
| 4,766,260 | 8/1988 | Manzer et al. | 570/168 |
| 4,827,055 | 5/1989 | Elsheikh | 570/160 |
| 4,861,744 | 8/1989 | Sobolev | 502/227 |
| 4,967,023 | 10/1990 | Carmello et al. | 570/166 |

FOREIGN PATENT DOCUMENTS

| | | |
|---|---|---|
| 0282005 | 8/1988 | European Pat. Off. . |
| 0298662 | 1/1989 | European Pat. Off. . |
| 0407961 | 1/1991 | European Pat. Off. . |
| 53-44509 | 12/1978 | Japan . |
| 62-44973 | 9/1987 | Japan . |
| 63-284135 | 11/1988 | Japan . |
| 2172933 | 7/1990 | Japan . |
| 1000485 | 8/1965 | United Kingdom . |

OTHER PUBLICATIONS

C. R. Acad. Sc. Paris, t 271 (Jul. 6, 1970) Baumer, et. al.
Inorg Chem, 5, pp. 1927–1933 D. B. Shinn, et al.
Journal of Catalysis, 33, pp. 39–46 H. J. Beitsma et al.
Anal. Chem., 29, p. 984 E. Staritzky et al.
Journal of Solid State Chemistry, 77 pp. 96–101 A. Le Bail et al.
Shinn, D. B. et al, *Inorg. Chem.*, 5, 1966, 1927–1933.
Reitsma, H. J. et al., *Journal of Catalysis*, 33, 39–46, 1974.
Moerkerken A. et al, *J. Catal.*, 24, 1972, pp. 177–180.

*Primary Examiner*—Alan Siegel

[57] ABSTRACT

A process is disclosed for producing HCFC-133a which includes reacting certain trihaloethene starting materials (e.g., trichloroethene) with HF in the gaseous phase at an elevated temperature in the presence of certain supported metal catalysts containing effective amounts of zinc. A catalyst of metal fluoride on a fluorinated alumina support having an atomic ratio of F to Al of at least 2.7:1 and containing β-aluminum fluoride, is employed.

20 Claims, No Drawings

PROCESS FOR THE MANUFACTURE OF 2-CHLORO-1,1,1-TRIFLUOROETHANE

This is a continuation of application Ser. No. 07/672,875 filed Mar. 20, 1991, now abandoned.

FIELD OF THE INVENTION

This invention relates to processes for the manufacture of saturated halohydrocarbons containing fluorine, and more particularly to gas-phase processes for producing 2-chloro-1,1,1-trifluoroethane (HCFC-133a) by catalytic fluorination of trihaloethenes.

BACKGROUND OF THE INVENTION

There has been considerable recent interest in halogen-substituted hydrocarbons containing flourine and hydrogen, particularly halogen-substituted ethanes. Many of these materials can be used as refrigerants, blowing agents, or as chemical starting materials for the production of refrigerants or blowing agents. Some such as $CF_3CH_2F$ (i.e., HFC-134a) are being considered to replace fully halogenated hydrocarbons containing chlorine which are less environmentally desirable due to their interaction with the earth's ozone layer.

Various processes have been disclosed for the production of halogen-substituted ethanes containing fluorine and hydrogen. For example, British Patent Specification 1,000,485 discloses a process for the preparation of organic fluorinated compounds (e.g., $CF_3CH_2Cl$ or $CF_3CHCl_2$) by fluorination of haloolefins (e.g., $CCl_2=CHCl$ or $CCl_2=CCl_2$) in a gaseous phase at an elevated temperature using an activated alumina (e.g., alumina activated by impregnation with a solution of one or more halides of polyvalent metals such as chromium, cobalt, nickel and manganese) which is partially fluorinated. U.S. Pat. No. 4,766,260 discloses a gas-phase process for the manufacture of $CF_3CHCl_2$ and $CF_3CHClF$ by fluorination of a suitable tetrahaloethylene (e.g., $CCl_2=CCl_2$) using a selected metal on a high fluorine content alumina support. U.S. Pat. No. 4,861,744 discloses the formation of $CF_3CH_2F$ (and $CF_3CH_2Cl$) by the vapor phase fluorination of a suitable trihaloethylene (e.g., $CCl_2=CHCl$) using a catalyst prepared by codepositing a hexavalent chromium oxide and a transition metal compound (e.g., titanium trichloride) on alumina followed by fluorinating the resulting combination. Japanese Patent Application Publication 2-172933 discloses a method for manufacturing $CF_3CH_2F$ by fluorinating $CF_3CH_2Cl$ in the presence of a fluorinating catalyst which contains a halide or oxide which contains chromium and at least one element selected from among aluminum, magnesium, calcium, barium, strontium, iron, nickel, cobalt and manganese (e.g., catalyst produced by adding a commercial alumina to a solution of chromium chloride, drying the mixture, and activating the residue using HF).

Aluminum fluoride may be obtained by the fluorination of alumina. Several phases of aluminum fluoride have been reported, each having a characteristic powder X-ray diffraction pattern.

$\alpha$-$AlF_3$ (i.e., alpha-aluminum fluoride) as reported by E. Staritzky and L. B. Asprey, *Anal. Chem.*, 29, 984 (1957) has a powder x-ray diffraction pattern characterized by various "d" spacings between 3.520 Angstroms and 1.560 Angstroms with the strongest intensity observed at a "d" spacing of 3.520 Angstroms. $\beta$-$AlF_3$ (i.e., beta-aluminum fluoride) as reported by U.S. Pat. No. 3,178,483 has a powder X-ray diffraction pattern characterized by various "d" spacings between 6.000 Angstroms and 1.558 Angstroms with very strong intensities observed at "d" spacings of 6.000 Angstroms and 3.563 Angstroms and strong intensities observed at "d" spacings of 3.465 Angstroms and 3.001 Angstroms. $\gamma$-$AlF_3$ (i.e., gamma-aluminum fluoride) as reported by U.S. Pat. No. 3,178,484 has a powder X-ray diffraction pattern characterized by various "d" spacings between 3.537 Angstroms and 1.623 Angstroms with very strong intensity observed at a "d" spacing of 3.537 Angstroms and a strong intensity observed at a "d" spacing of 1.768 Angstroms.

Processes using particular phases of $AlF_3$ have been disclosed. For example, European Patent Publication 0282005 discloses a process for preparing $CF_3CHCl_2$ (and $CF_3CHClF$) by reacting $CCl_2=CCl_2$ with HF in the gas phase in the presence of catalysts comprising $Cr_2O_3$ carried on $AlF_3$ in the gamma and/or beta form. Japanese Patent Application Publication 53-144509 discloses a process for the manufacture of 3,3,3-trifluoropropene using a catalyst bed comprising $\alpha$-aluminum fluoride and a second catalyst comprising other gas-phase fluorinating catalysts (e.g., $\beta$-aluminum fluoride and/or $\gamma$-aluminum fluoride).

SUMMARY OF THE INVENTION

It has been found that a catalyst of metal fluoride on a fluorinated alumina support having an atomic ratio of F to Al of at least 2.7:1 and containing $\beta$-aluminum fluoride can be prepared by fluorinating alumina (e.g., $\gamma$-$Al_2O_3$) which has been impregnated with a zinc halide; and that a trihaloethene of the formula $CX_2=CHCl$ wherein each X is chlorine or fluorine (e.g., $C_2HCl_3$) may be advantageously fluorinated with HF to 2-chloro-1,1,1-trifluoroethane (i.e., HCFC-133a) in the gaseous phase at an elevated temperature in the presence of a supported metal catalyst of this type wherein zinc is at least about 0.1 percent by weight of the catalyst and is from about 40 to 100 percent by weight of the metal on said support (said catalyst optionally containing one or more of other selected metals). Accordingly, a gaseous process for producing HCFC-133a is provided by this invention which comprises the step of reacting a trihaloethene of the formula $CX_2=CHCl$ (wherein each X is chlorine or fluorine) with HF in the gaseous phase at an elevated temperature in the presence of a supported metal catalyst; wherein said catalyst is a catalyst of metal fluoride on a fluorinated alumina support having an atomic ratio of F to Al of at least 2.7:1 and containing $\beta$-aluminum fluoride; wherein said supported metal includes zinc and optionally includes one or more other metals selected from Groups VIII, VIIB, VIB, IIIB, IIB and IB of the Periodic Table and elements having atomic numbers between 57 and 71; and wherein zinc is at least about 0.1 percent by weight of the catalyst and is at least about 40 percent by weight of the metal on said support.

DETAILS OF THE INVENTION

This invention provides a catalytic process for producing 2-chloro-1,1,1-trifluoroethane by the fluorination of a trihaloethene of the formula $CX_2=CHCl$ wherein each X is chlorine or fluorine. Starting materials include trichloroethene, 1,2-dichlorofluoroethene and 1-chloro-2,2-difluoroethene. Trichloroethene is preferred. The process uses a catalyst of metal fluoride on a fluorinated alumina support wherein the fluorinated alumina contains beta aluminum fluoride and wherein zinc is at least about 0.1 percent by weight (and preferably from about 1 to 10 percent by weight) of the catalyst.

In addition to zinc the supported metal may also include one or more other metals selected from Group VIII (e.g., Fe, Co and/or Ru), Group VIIB (e.g., Mn), Group VIB (e.g., Cr), Group IIIB (e.g., Y), Group IIB (e.g., Cd) and Group IB (e.g., Cu) of the Periodic Table and elements having atomic numbers between 57 and 71 (e.g., La, Ce and/or Nd). However zinc should be at least about 40 percent by weight of the metal on the support. Catalysts of this invention which consist essentially of a mixture of zinc fluoride and chromium fluoride on a fluorinated alumina support are considered particularly useful. The preferred catalysts of this invention consist essentially of zinc fluoride on a fluorinated alumina support.

By a fluorinated alumina support is meant a composition comprising aluminum, oxygen and fluorine in such proportions that the total fluorine content of the catalyst composition taken as $AlF_3$ corresponds to at least 90 weight percent, exclusive of the supported metal (i.e., the atomic ratio of F to Al in the support is at least 2.7). The remainder of the support may include aluminum oxide or aluminum oxyfluoride.

The high $AlF_3$ content support can be prepared in any manner known to the art. For example, the invention catalyst can be prepared by fluorination of alumina or aluminum oxyfluoride impregnated with a solution of a zinc compound or zinc and chromium compounds which may be in the form of any soluble compound of the metal such as the oxide, oxyhalide, halide, pseudohalide, nitrate, sulfate, or organic salt such as acetate, propionate and any other compound of said metals which is convertible to a metal fluoride under the reaction conditions described herein. The halides include chlorides, fluorides, and bromides. The pseudohalides include cyanides, cyanates and thiocyanates. The preferred metal is zinc; and the preferred catalyst preparation involves fluorination of $\gamma$-$Al_2O_3$ (i.e., gamma-alumina) which has been impregnated with a zinc halide.

The form of the catalyst is not critical and may be used in the form of pellets, powders or granules.

In addition, the catalyst composition can also be prepared by co-precipitation of the catalytic metal and the aluminum as the hydroxides which are thereafter dried and calcined to form the mixed oxides, a technique well known to the art. The resulting oxide can be fluorinated as described herein.

Generally, the catalyst composition of the present invention will be fluorinated by pretreatment with HF or other vaporizable compounds containing fluorine such as $SF_4$, $CCl_3F$, $CCl_2F_2$, $CHF_3$ or $CCl_2FCClF_2$ to activate the catalyst. This pretreatment is accomplished by placing the catalyst composition in a suitable container which can be the reactor to be used to perform the reaction of the instant invention, and thereafter, passing HF over the dried catalyst composition. This is conveniently carried out by passing HF over the catalyst for a period of time, for example, of about 15 to 300 minutes at a temperature of, for example, about 200° C. to 450° C. Pretreatment is preferred, but is not essential provided that initial process conditions and equipment are selected so as to fluorinate the catalyst under initial process conditions.

By vaporizable fluorine-containing compound is meant a fluorine-containing compound which will convert the catalyst of the instant invention to the desired degree of fluorination using the pretreatment conditions described herein.

A suitable catalyst may be prepared, for example, as follows:

A quantity of $\gamma$-$Al_2O_3$ is impregnated with a solution, usually aqueous, of a catalytically effective amount of a zinc compound or of compounds containing zinc and any other metal(s) to be included on the support (e.g., chromium). By catalytically effective amount is meant an amount of the metal which causes the production of the desired compounds in the process of the instant invention. Normally, this amount, expressed as metal, will be between about 0.1 and 50 weight percent of the alumina support, preferably not more than 20 weight percent, and more preferably from about 0.1 to 10 weight percent. The impregnated alumina can be dried until essentially all moisture is removed, e.g., for about 18 hours at about 400° C. The dried catalyst is then transferred to the reactor to be used. The temperature is then gradually increased to about 400° C. while maintaining a flow of $N_2$ through the reactor to remove any remaining traces of moisture from the catalyst and the reactor. The temperature is then lowered to about 200° C. and HF, or other vaporizable fluorine containing compounds such as $SF_4$, $CCl_3F$, $CCl_2F_2$, $CHF_3$ or $CCl_2FCClF_2$, diluted with $N_2$ is passed through the reactor. The $N_2$ flow can be gradually reduced until only HF, or other vaporizable fluorine containing compounds such as $SF_4$, $CCl_3F$, $CCl_2F_2$, $CHF_3$ or $CCl_2FCClF_2$, is being passed through the reactor. At this point the temperature can be increased to about 450° C. and held at that temperature to convert the impregnated $Al_2O_3$ to a fluorine content corresponding to at least 90% $AlF_3$ by weight, e.g., for 15 to 300 minutes, depending on the flow of the fluorine containing compound and the catalyst volume.

The reaction of a trihaloethene with HF in the presence of the catalyst of the instant invention is conducted in the gas phase at an elevated temperature. Suitable temperatures range from about 100° C. to 400° C. The reaction temperature is preferably from about 150° C. to 350° C., and is most preferably from about 175° C. to about 225° C. The contact time is generally from about 0.1 to about 60 seconds, and is preferably from about 5 to about 30 seconds.

The molar ratio of HF to the trihaloethene can range from about 1:1 to about 20:1, and is preferably from about 3:1 to 15:1, and more preferably from about 5:1 to 10:1.

In general, with a given catalyst composition and starting material, the higher the temperature, the greater the HF/trihaloethene mole ratio, and the longer the contact time, the greater is the degree of fluorination.

The reaction of the trihaloethene with HF may be conducted in any suitable reactor, including fixed and fluidized bed reactors. The reaction vessel should be constructed from materials which are resistant to the corrosive effects of hydrogen fluoride such as Inconel® nickel alloy and Hastelloy® nickel alloy.

Pressure is not critical. Atmospheric and superatmospheric pressures are the most convenient and are therefore preferred.

2-Chloro-1,1,1,trifluoroethane can be converted to 1,1,1,2-tetrafluoroethane, a useful refrigerant.

Practice of the invention will become further apparent from the following non-limiting Examples.

EXAMPLES

General Procedure for Fluorination

The reactor (0.5 inch ID, 12 inch long Inconel® nickel alloy tubing) was charged with the amount of catalyst either as 1/12" pellets or as −10/+20 ASTM Std. Sieve No. (850 mm–2000 mm) powder as described in the following examples, and placed in a sand bath. The bath was gradually heated to 400° C. while nitrogen gas at a flow rate of 100 mL/minute was passed through the reactor to remove traces of water. The temperature was lowered to 150° C. and HF and nitrogen gas (1:1 molar ratio) were passed through the reactor. The temperature was gradually raised to 425° C. and maintained there for 30 to 240 minutes. The fluorine content of the alumina-based catalyst compositions corresponded to an $AlF_3$ content, exclusive of the metal, of at least 90%. The temperature was then decreased to the indicated values and, thereafter, $CHCl=CC_{12}$ and HF flow were started. The flows of HF and trichloroethene were adjusted to give the indicated molar ratios and contact times.

The reactor effluent was sampled on-line using a 20 foot long, one-eighth inch diameter column containing Krytox® perfluorinated polyether on an inert support and a helium flow of 35 cc/minute. Gas chromatographic conditions were 70° for 3 minutes followed by a temperature programming to 180° at a rate of 6°/minute.

General Procedures for Characterization

X-Ray (Cu $K_\alpha$-radiation) powder diffraction patterns were obtained using a Phillips APD 3600 or a Phillips APD 3720 diffractometer equipped with a theta-compensating slit.

Based upon the X-ray powder diffraction patterns, the presence of $\beta$-$AlF_3$ phase was evaluated from the intensity of the peak observed at a "d" spacing of about 6.0 Å (present only in the $\beta$-form) relative to the intensity of the strongest peak observed, (i.e., $I_6/I_{max}$). The strongest peak was generally observed at a "d" spacing of from 3.5 to 3.6 Angstroms.

Chemical analyses were obtained using inductively coupled plasma spectrometry and potentiometric determination of fluorine using a fluoride selective electrode and computer controlled additions of a fluoride standard.

Comparative Example A

ZnO Catalyst

A commercial sample of ZnO was molded into 4" diameter pellets under 70–80 tons of pressure. The pellets were crushed and sieved to a –10/+20 ASTM Std. Sieve No. (850 mm–2000 mm) powder. The General Procedure for fluorination for the alumina-based catalysts was followed using 54.1 g (30 cc) of ZnO as the initial catalyst charge. The results of the reaction of HF with 1,1,2-trichloroethene are given in Table I.

The used catalyst (67.16 g) was recovered corresponding to a 23.9% weight gain on fluorination.

Comparative Example B $\gamma$-$Al_2O_3$ Catalyst

The General Procedure for fluorination was followed using 30 cc of $\gamma$-$Al_2O_3$ (1/12" extrudates) as the initial catalyst charge. The results of the reaction of HF with 1,1,2-trichloroethene are given in Table I.

The used catalyst (27.8 g) was recovered corresponding to a 44.8% weight gain on fluorination. The used catalyst had a characteristic powder X-ray diffraction pattern with $I_6/I_{max}$ averaging about 0.03. Chemical analysis gave an F:Al (atom ratio) averaging about 3.00:1 (about 100% conversion to $AlF_3$).

Example 1

2%Zn/$\gamma$-$Al_2O_3$ Catalyst

Dried (110° C. for a minimum of 16 hours) $\gamma$-$Al_2O_3$ (100 g, 1/12" extrudates) was added to a solution containing 4.16 g of $ZnCl_2$ in 85.70 g distilled water. The resulting material was dried at 110° C. overnight. The General Procedure for fluorination was followed using 19.00 g (30 cc) of 2%Zn/$\gamma$-$Al_2O_3$ as the initial catalyst charge. The results of the reaction of HF with 1,1,2-trichloroethene are given in Table I.

The used catalyst (29.43 g) was recovered corresponding to a 54.9% weight gain on fluorination. The used catalyst had a characteristic powder X-ray diffraction pattern with $I_6/I_{max}$ averaging about 0.11. Chemical analysis gave an F:Al (atom ratio) averaging about 2.90:1 (about 97% conversion to $AlF_3$) and a Zn:Al (atom ratio) averaging about 0.0199:1.

TABLE I

| Example | A | B | 1 |
|---|---|---|---|
| Initial Catalyst Charge | ZnO | $\gamma$-$Al_2O_3$ | 2% Zn/$\gamma$-$Al_2O_3$ |
| Temperature, °C. | 200 | 200 | 200 |
| HF/$CCl_2$=CHCl (Mole Ratio) | 6/1 | 6/1 | 6/1 |
| Contact Time, sec | 30 | 30 | 30 |
| Conversion, % | 1.0 | 6.8 | 89.2 |
| Selectivity to $CF_3CH_2Cl$, % | 6.2 | 33.8 | 98.3 |

These results clearly show the greater activity and selectivity of the 2%Zn/$\gamma$-$Al_2O_3$ compared to ZnO and $\gamma$-$Al_2O_3$ in the fluorination of 1,1,2-trichloroethene to HCFC-133a.

Comparative Example C

2%Co/$\gamma$-$Al_2O_3$

Dried (110° C., overnight) $\gamma$-$Al_2O_3$ (500 g, 1/12" extrudates) was added to a solution containing 40.35 g of $CoCl_2.6H_2O$ in 420 g distilled water. Excess water was evaporated by heating at approximately 110° C. overnight. The General Procedure for fluorination was followed using 21.66 g (30 cc) of 2%Co/$\gamma$-$Al_2O_3$ as the initial catalyst charge. The results of the reaction of HF with 1,1,2-trichloroethene after about 15 hours of operation are given in Table II.

The used catalyst had a characterized powder X-ray diffraction pattern with $I_6/I_{max}$ averaging about 0.12.

Chemical analysis gave an F:Al (atom ratio) averaging about 3.20:1 (about 107% conversion to $AlF_3$) and a Co:Al (atom ratio) averaging about 0.0217:1.

Comparative Example D

2%Cr/$\gamma$-$Al_2O_3$

Dried (110° C., overnight) $\gamma$-$Al_2O_3$ (200 g, 1/12" extrudates) was added to a solution containing 30.80 g of $Cr(NO_3)_3.9H_2O$ in 190 g distilled water. Excess water was evaporated by heating at approximately 110° C. overnight. The General Procedure for fluorination was followed using 21.94 g (30 cc) of 2%Cr/$\gamma$-$Al_2O_3$ as the initial catalyst charge. The results of the reaction of HF with 1,1,2-trichloroethene after about 15 hours of operation are given in Table II.

The used catalyst had a characteristic powder X-ray diffraction pattern with $I_6/I_{max}$ averaging about 0.07.

Chemical analysis gave an F:Al (atom ratio) averaging about 3.08:1 (about 103% conversion to $AlF_3$) and a Cr:Al (atom ratio) averaging about 0.0187:1.

Example 2

2%Zn/γ-Al₂O₃ Catalyst

The catalyst was prepared as described in Example 1. The results of the reaction of HF with 1,1,2-trichloroethene after about 15 hours of operation are given in Table II.

TABLE II

| Example | C | D | 2 |
|---|---|---|---|
| Initial Catalyst Charge | 2% Co/ γ-Al₂O₃ | 2% Cr/ γ-Al₂O₃ | 2% Zn/ γ-Al₂O₃ |
| Time on Stream (h:min) | 15:59 | 15:48 | 15:50 |
| Temperature, °C. | 200 | 200 | 200 |
| HF/CCl₂=CHCl (Mole Ratio) | 6/1 | 6/1 | 6/1 |
| Contact Time, sec | 30 | 30 | 30 |
| Conversion, % | 33.9 | 57.3 | 90.5 |
| Selectivity to CF₃CH₂Cl, % | 61.0 | 90.0 | 98.8 |

These results clearly show the greater activity and selectivity of the 2%Zn/γ-Al₂O₃ compared to 2%Co/γ-Al₂O₃ and 2%Cr/γ-Al₂O₃ in the fluorination of 1,1,2-trichloroethene to HCFC-133a.

Example 3

1%-Zn/γ-Al₂O₃

Dried (110° C., overnight) γ-Al₂O₃ (100 g, ¹⁄₁₂" extrudates) was added to a solution containing 2.08 g of ZnCl₂ in 77.61 g distilled water. The resulting material was dried at 110° C. overnight. The General Procedure for fluorination was followed using 18.13 g (30 cc) of 1%Zn/γ-Al₂O₃ as the initial catalyst charge. The results of the reaction of HF with 1,1,2-trichloroethene are given in Table III.

The used catalyst (26.41 g) was recovered corresponding to a 45.6% weight gain on fluorination. The used catalyst had a characteristic powder X-ray diffraction pattern with $I_6/I_{max}$ averaging about 0.11. Chemical analysis gave an F:Al (atom ratio) averaging about 2.81:1 (about 94% conversion to AlF₃) and a Zn:Al (atom ratio) averaging about 0.00991:1.

Example 4

4%Zn/γ-Al₂O₃

Dried (110° C. for a minimum of 16 hours) γ-Al₂O₃ (100 g, ¹⁄₁₂" extrudates) was added to a solution containing 8.32 g of ZnCl₂ in 74.65 g distilled water. The resulting material was dried at 110° C. overnight. The General Procedure for fluorination was followed using 18.79 g (30 cc) of 4%Zn/γ-Al₂O₃ as the initial catalyst charge. The results of the reaction of HF with 1,1,2-trichloroethene are given in Table III.

The used catalyst (29.43 g) was recovered corresponding to a 54.9% weight gain on fluorination. The used catalyst had a characteristic powder X-ray diffraction pattern with $I_6/I_{max}$ averaging about 0.19. Chemical analysis gave an F:Al (atom ratio) averaging about 2.99:1 (about 100% conversion to AlF₃) and a Zn:Al (atom ratio) averaging about 0.0362:1.

Example 5

10% Zn/γ-Al₂O₃

Dried (110° C. for a minimum of 16 hours) γ-Al₂O₃ (100 g, ¹⁄₁₂" extrudates) was added to a solution containing 20.8 g of ZnCl₂ in 90.95 g distilled water. The resulting material was dried at 100° C. overnight. The General Procedure for fluorination was followed using 24.98 g (30cc) of 10% Zn/γ-Al₂O₃ as the initial catalyst charge. The results of the reaction of HF with 1,1,2-trichloroethene are given in Table III.

The used catalyst (29.74 g) was recovered corresponding to a 23.0% weight gain on fluorination. The used catalyst had a characteristic powder X-ray diffraction pattern with $I_6/I_{max}$ averaging about 0.43. Chemical analysis gave an F:Al (atom ratio) averaging about 2.34:1 (about 78% conversion to AlF₃) and a Zn:Al (atom ratio) averaging about 0.0815:1.

TABLE III

| Example | 3 | 4 | 5 |
|---|---|---|---|
| Percent Zinc Loading | 1 | 4 | 10 |
| Temperature, °C. | 200 | 200 | 200 |
| HF/C₁₂C₂=CHCl (Mole Ratio) | 6/1 | 6/1 | 6/1 |
| Contact Time, sec | 30 | 30 | 30 |
| Conversion, % | 81.7 | 97.9 | 96.9 |
| Selectivity to CF₃CH₂Cl, % | 93.5 | 97.2 | 98.8 |

These results together with the results of Example 1 clearly show the consistently high activity and selectivity of the Zn/γ-Al₂O₃ system with various metal loadings for the fluorination of 1,1,2-trichloroethene to HCFC-133a.

Particular embodiments of the invention are included in the Examples. Other embodiments will become apparent to those skilled in the art from a consideration of the specification or practice of the invention. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the claims.

What is claimed is:

1. A process for producing 2-chloro-1,1,1-trifluoroethane comprising the step of reacting a trihaloethene of the formula CX₂=CHCl wherein each X is chlorine or fluorine, with HF in the gaseous phase at an elevated temperature in the presence of a supported metal catalyst; wherein said catalyst is a catalyst of metal fluoride on a fluorinated alumina support having an atomic ratio of F to Al of at least 2.7:1 and containing β-aluminum fluoride; wherein said supported metal includes zinc and optionally includes one or more other metals selected from Groups VIII, VIIB, VIB, IIIB, IIB and IB of the Periodic Table and elements having atomic numbers between 57 and 71; and wherein zinc is at least about 0.1 percent by weight of the catalyst and is at least about 40 percent by weight of the metal on said support.

2. The process of claim 1 wherein the catalyst is prepared by fluorinating γ-Al₂O₃ which has been impregnated with a zinc halide.

3. The process of claim 2 wherein the catalyst consists essentially of zinc fluoride on a fluorinated alumina support.

4. The process of claim 3 wherein the reaction is carried out at a temperature between about 100° C. and 400° C.

5. The process of claim 4 wherein zinc is from about 1 to 10 percent by weight of the catalyst.

6. The process of claim 5 wherein the trihaloethene is trichloroethene.

7. The process of claim 6 wherein the mole ratio of HF to trichloroethene is from about 3:1 to 15:1.

8. The process of claim 7 wherein the contact time is from about 0.1 to 60 seconds.

9. The process of claim 1 wherein the trihaloethene is selected from the group consisting of trichloroethene, 1,2-dichlorofluoroethene and 1-chloro-2,2-difluoroethene.

10. The process of claim 1 wherein the trihaloethene is trichloroethene.

11. The process of claim 1 wherein the mole ratio of HF to the trihaloethene is from about 1:1 to 20:1.

12. The process of claim 1 wherein the contact time is from about 0.1 to 60 seconds.

13. The process of claim 1 wherein the catalyst is prepared by impregnating gamma alumina with $ZnCl_2$ and fluorinating said impregnated alumina with HF.

14. The process of claim 1 wherein the supported metal further comprises chromium.

15. The process of claim 14 wherein the catalyst consists essentially of a mixture of zinc fluoride and chromium fluoride on a fluorinated alumina support.

16. A process for producing 2-chloro-1,1,1-trifluoroethane comprising the step of reacting a trihaloethene of the formula $CX_2$=CHCl wherein each X is chlorine or fluorine, with HF in the gaseous phase at an elevated temperature in the presence of a supported metal catalyst; wherein said catalyst is a catalyst of metal fluoride on a fluorinated alumina support having an atomic ratio of F to Al of at least 2.7:1 and containing β-aluminum fluoride; wherein said supported metal includes zinc and one or more other metals selected from Groups VIII, VIIB, VIB, IIIB, IIB and IB of the Periodic Table and elements having atomic numbers between 57 and 71; and wherein zinc is at least about 0.1 percent by weight of the catalyst and is at least about 40 percent by weight of the metal on said support.

17. The process of claim 16 wherein said supported metal includes one or more metals selected from Group VIII of the Periodic Table.

18. The process of claim 16 wherein said supported metal includes Co.

19. The process of claim 16 wherein said supported metal includes one or more metals selected from Group IB.

20. The process of claim 16 wherein said supported metal includes Cu.

* * * * *